United States Patent
Van Lier et al.

(10) Patent No.: US 10,919,787 B2
(45) Date of Patent: Feb. 16, 2021

(54) PROCESS USING ION EXCHANGE RESINS FOR THE TREATMENT OF WASTEWATER EMANATING FROM PURIFIED TEREPHTHALIC ACID PRODUCTION

(71) Applicant: SABIC Global Technologies B.V., Bergen op Zoom (NL)

(72) Inventors: Roy Van Lier, Sittard (NL); Syed Azhar Hashmi, Hyderabad (IN); Vadlamani Prasad Rao Chaitanya, Yanbu (SA); Sandeep P. Mohandas, Yanbu (SA); Muhammad Mosleh Al-Subhi, Yanbu (SA); Lee Sangjoo, Yanbu (SA); Hasan Mohammed Rashad Haneef, Yanbu (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 51 days.

(21) Appl. No.: 15/774,612

(22) PCT Filed: Nov. 8, 2016

(86) PCT No.: PCT/IB2016/056724
§ 371 (c)(1),
(2) Date: May 9, 2018

(87) PCT Pub. No.: WO2017/081610
PCT Pub. Date: May 18, 2017

(65) Prior Publication Data
US 2018/0346350 A1    Dec. 6, 2018

Related U.S. Application Data

(60) Provisional application No. 62/255,084, filed on Nov. 13, 2015.

(51) Int. Cl.
  C02F 1/42    (2006.01)
  C02F 1/66    (2006.01)
  (Continued)

(52) U.S. Cl.
  CPC ............... C02F 1/42 (2013.01); B01J 41/04 (2013.01); B01J 41/05 (2017.01); B01J 41/07 (2017.01);
  (Continued)

(58) Field of Classification Search
  None
  See application file for complete search history.

(56) References Cited

U.S. PATENT DOCUMENTS 4,540,493 A    9/1985   Dickerson et al.
5,107,002 A    4/1992   Shih
(Continued)

FOREIGN PATENT DOCUMENTS

CN    85101740 A    1/1987
CN    1159231 C    7/2004
(Continued)

OTHER PUBLICATIONS

"Expansion of PTA Capacity at IRHR Rotterdam plant"; Date of Publication: May 20, 2011; Netherlands;2 pages.
(Continued)

Primary Examiner — Hayden Brewster
(74) Attorney, Agent, or Firm — Cantor Colburn LLP

(57) ABSTRACT

A method for recovering water from purified terephthalic acid production wastewater includes: producing purified terephthalic acid comprising purified terephthalic acid feedstock and wastewater comprising impurities; separating the purified terephthalic acid feedstock from the wastewater comprising impurities; transferring the wastewater to a tank; adjusting the p H of the wastewater with a basic solution;
(Continued)

adjusting the temperature of the wastewater; passing the wastewater to a column; contacting the wastewater with an ion exchange resin to remove the impurities; and recovering the water depleted of impurities.

20 Claims, 2 Drawing Sheets

(51) Int. Cl.

| | |
|---|---|
| B01J 47/02 | (2017.01) |
| B01J 49/57 | (2017.01) |
| B01J 49/07 | (2017.01) |
| B01J 41/05 | (2017.01) |
| B01J 47/04 | (2006.01) |
| B01J 41/04 | (2017.01) |
| C07C 51/42 | (2006.01) |
| B01J 41/07 | (2017.01) |
| B01J 41/12 | (2017.01) |
| C02F 103/36 | (2006.01) |
| C02F 103/38 | (2006.01) |
| C02F 101/32 | (2006.01) |

(52) U.S. Cl.
CPC ............ *B01J 41/12* (2013.01); *B01J 47/02* (2013.01); *B01J 47/04* (2013.01); *B01J 49/07* (2017.01); *B01J 49/57* (2017.01); *C02F 1/66* (2013.01); *C07C 51/42* (2013.01); *C02F 2001/422* (2013.01); *C02F 2101/32* (2013.01); *C02F 2103/36* (2013.01); *C02F 2103/38* (2013.01); *C02F 2209/02* (2013.01)

(56) References Cited

U.S. PATENT DOCUMENTS

| | | | |
|---|---|---|---|
| 5,180,526 A | 1/1993 | Holderness | |
| 5,304,676 A | 4/1994 | Hindmarsh et al. | |
| 8,268,131 B2 | 9/2012 | Jang et al. | |
| 2009/0018361 A1 | 1/2009 | Numata et al. | |
| 2010/0249457 A1* | 9/2010 | Jang ................... | C07C 51/48 562/608 |
| 2013/0331603 A1* | 12/2013 | Martins ............... | C07C 51/43 562/485 |

FOREIGN PATENT DOCUMENTS

| | | |
|---|---|---|
| CN | 10680195 A | 10/2005 |
| CN | 100400432 U | 7/2008 |
| CN | 102863133 A | 1/2013 |
| CN | 102874955 A | 1/2013 |
| CN | 102910761 A | 2/2013 |
| CN | 102923663 A | 2/2013 |
| CN | 103140266 A | 6/2013 |
| CN | 103241857 B | 8/2013 |
| CN | 103663758 A | 3/2014 |
| CN | 1036933772 A | 4/2014 |
| JP | 2000070934 A | 3/2000 |
| KR | 20060092662 A | 8/2006 |
| KR | 20130012768 A | 2/2013 |
| WO | 2009115888 A1 | 9/2009 |
| WO | 2010008055 A1 | 1/2010 |

OTHER PUBLICATIONS

"Reliance chooses WABAG for effluent treatment and recycling facility for its PTA wastewater at Dahej, Gujarat for aggregate value of Rs. 270 crores (Euro 41.5 million)", 1 page.
Chinese Patent No. 102863133; Date of Publication: Jan. 9, 2013; Abstract Only, 2 pages.
Chinese Patent No. 102874955; Date of Publication: Jan. 16, 2013; Abstract Only, 1 page.
Chinese Patent No. 102910761; Date of Publication: Feb. 6, 2013; Abstract Only; 2 pages.
Chinese Patent No. 102923663; Date of Publication: Feb. 13, 2013; Abstract Only; 1 page.
Dow Film Tec Membrane: "FilmTec Elements Key to Success of Integrated Membrane-Based Reclamation System in Major Petrochemical Plant in Taiwan"; 6 pages.
International Search Report for International Application No. PCT/162016/056724; dated Jan. 13, 2017; 5 pages.
Japanese Patent No. 2000070934; Date of Publication: Mar. 7, 2000; Abstract Only, 2 pages.
Korean Patent No. 20060092662; Date of Publication: Aug. 23, 2006; Machine Translation, 9 pages.
Korean Patent No. 20130012768; Date of Publication: Feb. 5, 2013; Abstract Only, 2 pages.
Machine Translation for Chinese Patent No. 100400432; Date of Publication: Jul. 9, 2008; 8 pages.
Machine Translation for Chinese Patent No. 103140266; Date of Publication: Jun. 5, 2013; 27 pages.
Machine Translation for Chinese Patent No. 1159231; Date of Publication: Jul. 28, 2004; 7 pages.
Stewart, John M. et al., "Anaerobic treatability of selected organic toxicants in petrochemical wastes", Water Research, 1995, vol. 29, Issue 12, pp. 2730-2738.
Wong, Joseph M., "The History and Present Status of the World's First Major Membrane-Based Water Reuse System in the Petrochemical Industry", Water Environment Federation, 2012, 10 pages.
Written Opinion of the International Search Report for International Application No. PCT/IB2016/056724; dated Jan. 13, 2017; 6 pages.
European Search Report for European Application No. 16801047.8, Application Filing Date May 24, 2018; dated Mar. 24, 2020; 5 pages.
China Office Action and Search Report for China Application No. 2016800662199; Application Filing Date: Nov. 8, 2016; dated Aug. 4, 2020, 17 pages, with English Translation.

* cited by examiner

PROCESS USING ION EXCHANGE RESINS FOR THE TREATMENT OF WASTEWATER EMANATING FROM PURIFIED TEREPHTHALIC ACID PRODUCTION

CROSS REFERENCE TO RELATED APPLICATIONS

This application is a 371 of International Application No. PCT/IB2016/056724, filed Nov. 8, 2016, which claims priority to U.S. Application No. 62/255,084, filed Nov. 13, 2015, both of which are incorporated herein by reference in their entirety.

BACKGROUND

In processes for the production of Purified Terephthalic Acid (PTA), large quantities of water can be used, particularly as a solvent or wash liquid during the purification of the terephthalic acid product. An accumulation of impurities in the water renders the water unacceptable for reuse in the process without treatment. For example, para-toluic acid can be a troublesome impurity due to its low solubility and stickiness of resulting deposits. For reasons of impurity control, a portion of the water used in the PTA production process has to be discarded as wastewater.

In commercial PTA production processes, approximately 3 to 4 cubic meters of wastewater are produced for every ton of PTA manufactured, with the wastewater having a chemical oxygen demand (COD) of approximately 10,000 milligrams per Liter (mg/L) (ppm). COD analyses can be used to indirectly measure the amount of organic compounds or constituents in water, and therefore water quality with respect to organic impurities. Manufacturers worldwide produce hundreds of thousands of metric tons of PTA per year. Over time, wastewater associated with these production rates represents considerable losses both from resource and economic perspective.

A broad range of structurally diverse aromatic dicarboxylic acids can be efficiently and selectively extracted from the aqueous solution in a PTA production process by using a non-ionic polystyrene resin.

When wastewater which contains terephthalic acid is anaerobically treated, sulfuric acid radicals are added to the wastewater to be anaerobically treated, so that the wastewater comes to have a sulfuric acid ion concentration of 5-200 mg/L. The addition of a given amount of sulfuric acid radicals to terephthalic-acid-containing wastewater to be anaerobically treated can improve the efficiency of terephthalic acid decomposition by the anaerobic treatment. It is preferred that sulfuric acid radicals be added so as to result in a content thereof of 10 mass % or more of the terephthalic acid contained in the wastewater.

The wastewater can also be treated by a three-stage activated sludge process that can allow for a high removal percentage of organic impurities, e.g., greater than or equal to 90%. While this process has been demonstrated to be capable of high treatment loads and treatment of acidic effluent without neutralization, there are numerous drawbacks to the process. Disadvantages of the three-stage activated sludge process include a large footprint (e.g., large bioreactors), a long hydraulic retention time (e.g., several days), a high air injection (energy) requirement, the risk of sludge bulking, and an elevated consumption of anhydrous ammonia and phosphoric acid. The latter have to be added to PTA process effluent since this is limited in nitrogen and phosphorous as macronutrients for the biomass assimilating the carbon values contained in the organic impurities in the wastewater.

Thus, with an outlook for increasing demands for PTA and increased PTA production, there is a need for a more economical wastewater treatment technology to be used in its production.

BRIEF DESCRIPTION

Disclosed herein, in various embodiments, are methods for treating wastewater emanating from purified terephthalic acid production.

A method for recovering water from purified terephthalic acid production wastewater comprises: producing purified terephthalic acid comprising purified terephthalic acid feedstock and wastewater comprising impurities; separating the purified terephthalic acid feedstock from the wastewater comprising impurities; transferring the wastewater to a tank; adjusting the pH of the wastewater with a basic solution; adjusting the temperature of the wastewater; passing the wastewater to a column; contacting the wastewater with an ion exchange resin to remove the impurities; and recovering the water depleted of impurities.

A method for recovering water from purified terephthalic acid production wastewater comprises: producing purified terephthalic acid comprising purified terephthalic acid feedstock and wastewater comprising impurities; separating the purified terephthalic acid feedstock from the wastewater comprising impurities; transferring the wastewater to a tank; adjusting the pH of the wastewater to 5 to 9 with a basic solution; adjusting the temperature of the wastewater to 25 to 50° C.; passing the wastewater to a column; contacting the wastewater with an ion exchange resin to remove the impurities; and recovering the water depleted of impurities.

A method for recovering water from purified terephthalic acid production wastewater, comprising: producing purified terephthalic acid comprising purified terephthalic acid feedstock and wastewater comprising impurities selected from para-toluic acid, trimellitic acid, terephthalic acid, orthophthalic acid, benzoic acid, acetic acid, or a combination comprising at least one of the foregoing; separating the purified terephthalic acid feedstock from the wastewater comprising impurities; transferring the wastewater to a tank; adjusting the pH of the wastewater to 5 to 9; adjusting the temperature of the wastewater to 25° C. to 50° C.; passing the wastewater to a column; contacting the wastewater with an ion exchange resin to remove the impurities; recovering the water depleted of impurities, wherein the water depleted of impurities contains at least 99% less acidic impurities as compared to wastewater not treated with an ion exchange resin; regenerating the ion exchange resin with dilute sodium hydroxide; wherein the method is carried out at a pressure of 0.1 MegaPascal to 0.3 MegaPascal.

These and other features and characteristics are more particularly described below.

BRIEF DESCRIPTION OF THE DRAWINGS

The following is a brief description of the drawings wherein like numbers are numbered alike and which are presented for purposes of illustrating the exemplary embodiments disclosed herein and not for the purposes of limiting the same.

DETAILED DESCRIPTION

Figure 1:
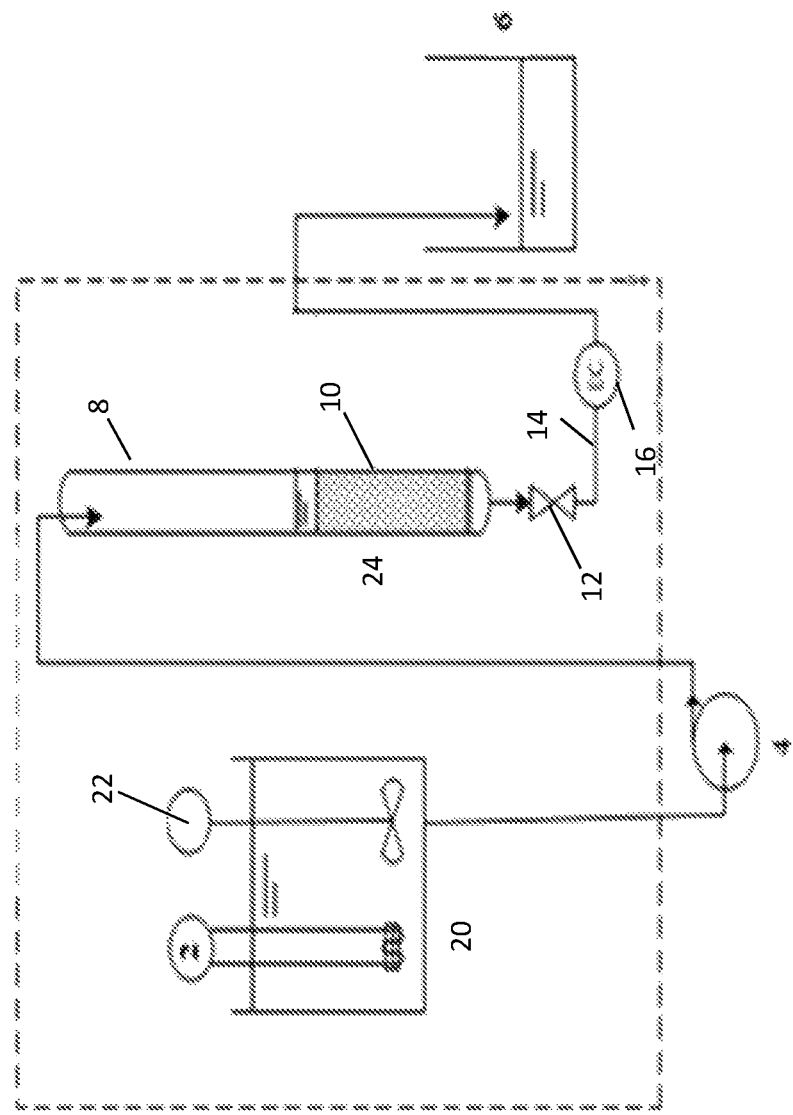
FIG. 1 is a schematic drawing of a test setup for the recovery of water from wastewater emanating from the production of purified terephthalic acid.

Disclosed herein are methods for recovering water from wastewater formed during Purified Terephthalic Acid (PTA) production using ion exchange resins. A major advantage of this approach is that it can treat effluents close to where they originate in the production process. Such effluents can be much more concentrated than in the case of biological end-of-pipe treatment, which, for reason of dilution, can require mixing of various wastewater streams. Other disadvantages of the biological treatment route include long hydraulic residence times (i.e., 3-5 days), along with high air injection requirements (i.e., energy), possibility of sludge bulking and high consumption of anhydrous ammonia and phosphoric acid which have to be added to the PTA effluent limited in nitrogen and phosphorous as macronutrients for the biomass.

The treated water can be reused within the PTA production process. Constituents for use in the PTA production process have the potential to be recovered from the wastewater, e.g., terephthalic acid, precursors of terephthalic acid, or a combination comprising at least one of the foregoing. For example, the method disclosed herein can remove acid impurities, e.g., para-toluic acid, from terephthalic acid production wastewater using an ion exchange resin. The ion exchange resin can include an anion exchange resin, e.g., a weakly basic anion exchange resin, a strongly basic anion exchange resin, or a combination comprising at least one of the foregoing.

During PTA production, PTA feedstock and wastewater comprising impurities are produced. The wastewater can include impurities such as para-toluic acid and other carboxylic acid impurities. The PTA feedstock can be separated from the wastewater comprising impurities, and the wastewater can be transferred to a tank to undergo treatment and allow water to be recovered. Treatment of the wastewater can include adjusting the wastewater's pH (e.g., with addition of a basic solution), adjusting the wastewater's temperature, or a combination comprising at least one of the foregoing. For example, the wastewater can be contacted with the ion exchange resin at a temperature of 10° C. to 60° C., for example, 25° C. to 50° C., for example, 30° C. to 45° C. The pH of the wastewater can be adjusted to 4 to 10 with the basic solution. After temperature and/or pH adjustment, the wastewater can be passed to a column where the wastewater can then be contacted with an ion exchange resin within the column to remove impurities contained in the wastewater. It can be desirable in the method disclosed herein to include a feed that is either free or contains a negligible load of suspended solids, i.e., less than 5 kilograms (kg) suspended solids per square meter of resin bed surface per loading cycle. This is because solids can foul the resin bed and therefore can deteriorate the resin bed's performance. Hence, it can be desirable to subject wastewater emanating from the PTA process to solid/liquid separation (e.g., a filtration stage) before feeding into the ion exchange process disclosed herein.

Water depleted of impurities can be recovered as an eluate emanating from the column. The methods disclosed herein can be carried out to remove acidic impurities, for example para-toluic acid (4-methylbenzoic acid), benzoic acid, ortho-phthalic acid (benzene-1,2-dicarboxylic acid), terephthalic acid (benzene-1,4-dicarboxylic acid), trimellitic acid (benzene-1,2,4-tricarboxylic acid) and acetic acid, among others, from wastewater using, for example, weakly or strongly basic ion exchange resins. It is possible to remove the acidic impurities in their deprotonated forms, i.e., as carboxylate anions.

The process, wherein the wastewater is contacted with the ion exchange resin in the column to remove impurities can be conducted at a pressure of 0.01 MegaPascal (MPa) to 2 MPa, for example, 0.1 MPa to 0.3 MPa.

Impurity removal can be tuned to any desirable percentage. For example, the water depleted of impurities can contain, for example, 0.01 ppm to 500 ppm of total acidic impurities after being contacted with the ion exchange resin, for example, 0.05 ppm to 250 ppm, for example, 1 ppm to 100 ppm. For example, the water depleted of impurities can contain 0.1 ppm to 10 ppm para-toluic acid; 1 ppm to 10 ppm benzoic acid; 1 ppm to 10 ppm acetic acid. After being contacted with the ion exchange resin, the water depleted of impurities can contain at least 99% less acidic impurities, for example, at least 99.5% less acidic impurities, and for example, at least 99.9% less acidic impurities. For example, the water depleted of impurities can comprise 30% to 80% less acidic impurities after contact with the ion exchange resin.

Large quantities of water can be used during PTA production, for example as a solvent or wash liquid, during the purification of the terephthalic acid product. Due to the build-up of impurities in the water during the process, the resultant wastewater can be difficult to reuse in the process without treatment. For example, para-toluic acid can become a problematic impurity because of its low solubility and stickiness when deposited. Further, without any treatment and/or reuse of the wastewater, there can be a potential loss for useful constituents that are contained therein, for example, terephthalic acid, its precursors, or a combination comprising at least one of the foregoing. The methods disclosed herein can provide solutions to overcome these problems during PTA production, for example, the recovery of water and potential recovery of useful constituents to be reused in the process.

The wastewater to be treated can be a filtrate, e.g., so-called first-stage filtrate, emanating from the terephthalic acid purification process. Wastewater emanating from PTA production can contain carboxylic acids. For example, the wastewater can contain para-toluic acid, benzoic acid, ortho-phthalic acid, terephthalic acid, trimellitic acid, acetic acid, or a combination comprising at least one of the foregoing. Other exemplary impurities common to the PTA process which can be contained in the wastewater can include 4-carboxybenzaldehyde (4-CBA, 4-formylbenzoic acid), benzil (1,2-difenylethane-1,2-dione), fluorenone (fluoren-9-one), among others, or a combination comprising at least one of the foregoing.

According to the methods disclosed herein, an ion exchange resin can be used for removing acidic impurities from the wastewater generated during PTA production. Ion exchange resins can be desirable due to their ability to be regenerated and reused, their high functionality allowing them to be modified and made for use in various industrial applications ranging from water softening, water demineralization, resource recovery to product purification, and their cost effectiveness. Ion exchange resins for use in the methods disclosed herein can include resins having a matrix comprising polystyrene, aliphatic polyamine, mixed polyalkylene amine, styrene divinyl benzene copolymers, resins containing amine or dimethyl amine functional groups, amine derivative resins, or a combination comprising at least one of the foregoing. As previously described herein, the ion exchange resin can include a weakly basic ion exchange resin, a strongly basic ion exchange resin, or a combination comprising at least one of the foregoing. A basic ion exchange resin can be selected to allow carboxylate anions to be exchanged with ions released from the resin beads in a way that maintains electroneutrality. A model reaction for this ion exchange process is shown in equation (1):

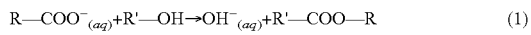

$$R\text{—}COO^-_{(aq)} + R'\text{—}OH \rightarrow OH^-_{(aq)} + R'\text{—}COO\text{—}R \qquad (1)$$

wherein:

R—COO⁻ represents e.g., acetate, benzoate and p-toluate and

R' represents the resin structure.

Fully deprotonated terephthalic and trimellitic acid exchange with 2 and 3 OH⁻, respectively.

The anion exchange resins disclosed herein do not remove dissolved metals such as cobalt and manganese originating from PTA catalysts. These could be removed in a post-treatment stage using cationic resins, however, depending on the point of reuse of the water treated by anion exchange, it can be more beneficial to not extract them.

The ion exchange method disclosed herein does not remove non-ionic, apolar impurities such as benzil or fluorenone. For example, these could be removed by passing the wastewater through a granular activated carbon (GAC) bed.

Exemplary ion exchange resins for use in the methods disclosed herein include the weakly basic anion resin designated Dow AMBERLYST™ A21 and the strongly basic anion resin designated LEWATIT™ MonoPlus MP 500 manufactured by Lanxess.

The ion exchange resin used for the removal of impurities can be regenerated using a basic solution when it becomes exhausted. The basic solution can include a caustic soda solution, e.g., a dilute (about 2 to about 4 wt %) caustic soda solution. For example, the basic solution can be selected from sodium hydroxide (e.g., dilute sodium hydroxide as a 2-4 wt % solution), sodium carbonate, ammonia, potassium hydroxide, potassium carbonate or a combination comprising at least one of the foregoing. After being used to regenerate the ion exchange resin, the carboxylic acid-containing regenerant solution can be utilized for pH control or disposed of in subsequent wastewater treatment processes.

A more complete understanding of the components, processes, and apparatuses disclosed herein can be obtained by reference to the accompanying drawings. These figures (also referred to herein as "FIG.") are merely schematic representations based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

Referring to FIG. 1, a laboratory apparatus and process for the removal of dissolved impurities, e.g., carboxylic acids, and recovery of water from PTA production wastewater is illustrated. As illustrated in FIG. 1, the method can employ a feed tank 20 to contain the wastewater comprising impurities after being separated from the PTA feedstock. The feed tank can further comprise a stirrer 22 for homogenizing the contents therein and a heater 2 for adjusting the temperature of the wastewater.

The pH of the wastewater contained in feed tank 20 can be adjusted depending on the process conditions desired. For example, the pH of the wastewater can be adjusted to 4 to 10. The pH adjustment of the wastewater can be carried out using a basic solution comprising sodium hydroxide, potassium hydroxide, or dilutions and/or combinations comprising at least one of the foregoing.

The temperature of the wastewater in feed tank 20 can be adjusted with heater 2 to meet desired process conditions. For example, the temperature of the wastewater can be adjusted such that it is contacted with the ion exchange resin at a temperature of 10° C. to 60° C., for example, 25° C. to 50° C.

The wastewater can be fed to a top portion 8 of column 24 using, for example, a pump 4 or any other means of transfer. Within the column 24, the wastewater can be contacted with an ion exchange resin in an ion exchange resin bed 10. As the wastewater is contacted with the ion exchange resin bed 10, carboxylate anions in the water can be exchanged against the ions released from the resin beads, collectively or selectively removing impurities (e.g., carboxylic acids) contained in the wastewater. The eluate, i.e., water depleted of impurities, can pass through the bottom of column 24, valve 12, line 14, and via specific conductivity probe 16. The water depleted of impurities can then be collected and recovered using a second tank 6. At industrial scale, the recovered water can be reused in the terephthalic production process, with or without further treatment.

During the stage where the wastewater is passed through the column 24 and contacted with the ion exchange resin bed 10, the ion exchange process can be tuned by, for example, varying the hydraulic parameters, selection of resins, etc., to separate the aromatic from the non-aromatic acids, more specifically aromatic carboxylic acids from aliphatic carboxylic acids, or to separate mono from di/triacids. The aromatic carboxylic acids can include para-toluic acid, trimellitic acid, phthalic acid (in ortho or para form), benzoic acid, or a combination comprising at least one of the foregoing. The aliphatic acid can include acetic acid, acrylic acid, propionic acid, or a combination comprising at least one of the foregoing.

The majority of the apparatus components described above can be placed inside an incubator (graphically represented by dashed lines in FIG. 1) for experiments at a set temperature above ambient.

The process, wherein the wastewater is contacted with the ion exchange resin in the column to remove impurities can be conducted at a pressure of 0.01 MPa to 2 MPa, for example, 0.1 MPa to 0.3 MPa.

The water recovered by the methods disclosed herein is partially or completely depleted of carboxylic acid impurities and can be reused in the PTA production process with or without further treatment. The water depleted of impurities can contain, for example, 0.01 ppm to 500 ppm of acidic impurities after being contacted with the ion exchange resin, for example, 0.05 ppm to 250 ppm, for example, 1 ppm to 100 ppm. For example, the water depleted of impurities can contain 0.1 ppm to 10 ppm para-toluic acid; 1 ppm to 10 ppm benzoic acid; 1 ppm to 100 ppm acetic acid. After being contacted with the ion exchange, the water depleted of impurities can contain at least 99% less acidic impurities, for example, at least 99.5% less acidic impurities, and for example, at least 99.9% less acidic impurities. Further, the methods disclosed herein can be tuned to remove specified amounts of impurities from wastewater. For example, the water depleted of impurities can comprise 30% to 80% less acidic impurities after contact with the ion exchange resin. The following examples are merely illustrative of the method disclosed herein and are not intended to limit the scope hereof.

EXAMPLES

Example 1

Batches of 20 L of synthetic test solution were prepared using demineralized water and reagent-grade chemicals. The test solution contained 320 mg/L, 256 mg/L, and 288 mg/L of para-toluic acid, benzoic acid, and acetic acid, respectively, as well as other impurities common to the PTA production process, such as cobalt, bromide and others. The pH of the wastewater was adjusted to either 5 or 9 using dilute sodium hydroxide (NaOH). Tests were carried out at ambient (25° C.) or elevated (50° C.) temperature. The test solution was fed to the column and passed through the resin bed containing an ion exchange resin (AMBERLYST™ A21, commercially available from Dow). The resulting water was collected and the residual carboxylic acid concentrations in the eluate were determined using ion chromatography.

Table 1 shows concentrations of carboxylic acids in the eluate obtained with test solution at a pH of 5, a temperature of 25° C. and a column feed rate of 25 bed volumes per hour (BV/h)—the resin bed volume used was 120 mL. The cumulative amount of test solution passed through the column was measured in milliliters (mL) and the acid concentrations in the eluate were measured in milligrams per Liter (mg/L).

TABLE 1

| Cum. qty. of water passed through column (BV[1]) | p-TA[2] (mg/L) | BA[3] (mg/L) | AA[4] (mg/L) |
|---|---|---|---|
| 0 | 320 | 256 | 288 |
| 4.1 | 3.6 | 3.7 | 0.3 |
| 10.3 | 1.6 | 1.8 | 210 |

[1]Bed Volume;
[2]para-Toluic Acid;
[3]Benzoic Acid;
[4]Acetic Acid

Table 2 shows concentrations of carboxylic acids in the eluate obtained with test solution at a pH of 9, a temperature of 25° C. and a column feed rate of 25 BV/h:

TABLE 2

| Cum. qty. of water passed through column (BV[1]) | p-TA[2] (mg/L) | BA[3] (mg/L) | AA[4] (mg/L) |
|---|---|---|---|
| 0 | 320 | 256 | 288 |
| 1.4 | 1.1 | 1.2 | 8.0 |
| 7.7 | 6.0 | 6.2 | 310 |

[1]Bed Volume;
[2]para-Toluic Acid;
[3]Benzoic Acid;
[4]Acetic Acid

The above results demonstrate that initially both aliphatic and aromatic acids are virtually quantitatively removed, both at pH 5 and pH 9. With longer times the aliphatic acid, acetic acid, preferentially desorbs. Therefore, the method disclosed herein makes it also possible to separate aromatic carboxylic acids from non-aromatic carboxylic acids.

Example 2

Batches of 20 L of synthetic test solution were prepared using demineralized water and reagent-grade chemicals. The test solution contained 378 mg/L para-toluic acid, 251 mg/L benzoic acid, 50 mg/L acetic acid, 76 and 50 mg/L para- and ortho-phthalic acid, respectively, and 50 mg/L trimellitic acid as well as other impurities common to the PTA production process, such as cobalt, bromide and manganese. The pH of the wastewater was adjusted to 5 using dilute sodium hydroxide (NaOH). The test temperature was controlled at 50° C. by placing most of the experimental setup inside an incubator. The test solution was fed to the column and passed through the resin bed containing an ion exchange resin (LEWATIT® MonoPlus MP 500, commercially available from Lanxess). The ion exchange resin bed volume was 120 mL. Eluate samples were analyzed for (i) total organic carbon (TOC) concentration, and (ii) residual acid concentrations using liquid chromatography-diode array detection-mass spectrometry (LC-DAD-MS).

Table 3 summarizes the results obtained with test solution of pH 5, a temperature of 50° C. and a column feed rate of 25 BV/h. The cumulative amount of test solution passed through the column was measured in milliliters (mL), the acid concentrations in the eluate were measured in milligrams per Liter (mg/L), and TOC determined as milligrams of carbon per Liter (mg C/L).

TABLE 3

| Sample No. | BV[1] | TOC[2] (mg C/L) | AA[3] (mg/L) | BA[4] (mg/L) | p-TA[5] (mg/L) | PHA[6] (mg/L) | TA[7] (mg/L) | TMA[8] (mg/L) |
|---|---|---|---|---|---|---|---|---|
| 1 | 12 | <1 | <1 | <0.05 | <0.05 | <0.01 | <0.01 | <0.5 |
| 2 | 39 | <1 | <1 | <0.05 | <0.05 | <0.01 | <0.01 | <0.5 |
| 3 | 86 | 50 | 160 | 24 ± 1 | 25 ± 1 | <0.01 | <0.01 | <0.5 |
| 4 | 111 | 390 | 65 | 280 ± 14 | 340 ± 21 | <0.01 | <0.01 | <0.5 |
| Stock | — | ~540 | 50 | 251 | 378 | 50 | 76 | 50 |

[1]Bed Volume;
[2]Total Organic Carbon;
[3]Acetic Acid;
[4]Benzoic Acid;
[5]para-Toluic Acid;
[6]PHthalic Acid;
[7]Terephthalic Acid;
[8]TriMellitic Acid The above results demonstrate that it is not only possible to quantitatively remove both aliphatic and aromatic acids, but that the method disclosed herein can be tuned to separate aromatic carboxylic acids from non-aromatic carboxylic acids, and/or to separate monocarboxylic acids from di/tri-carboxylic acids.

Figure 2:
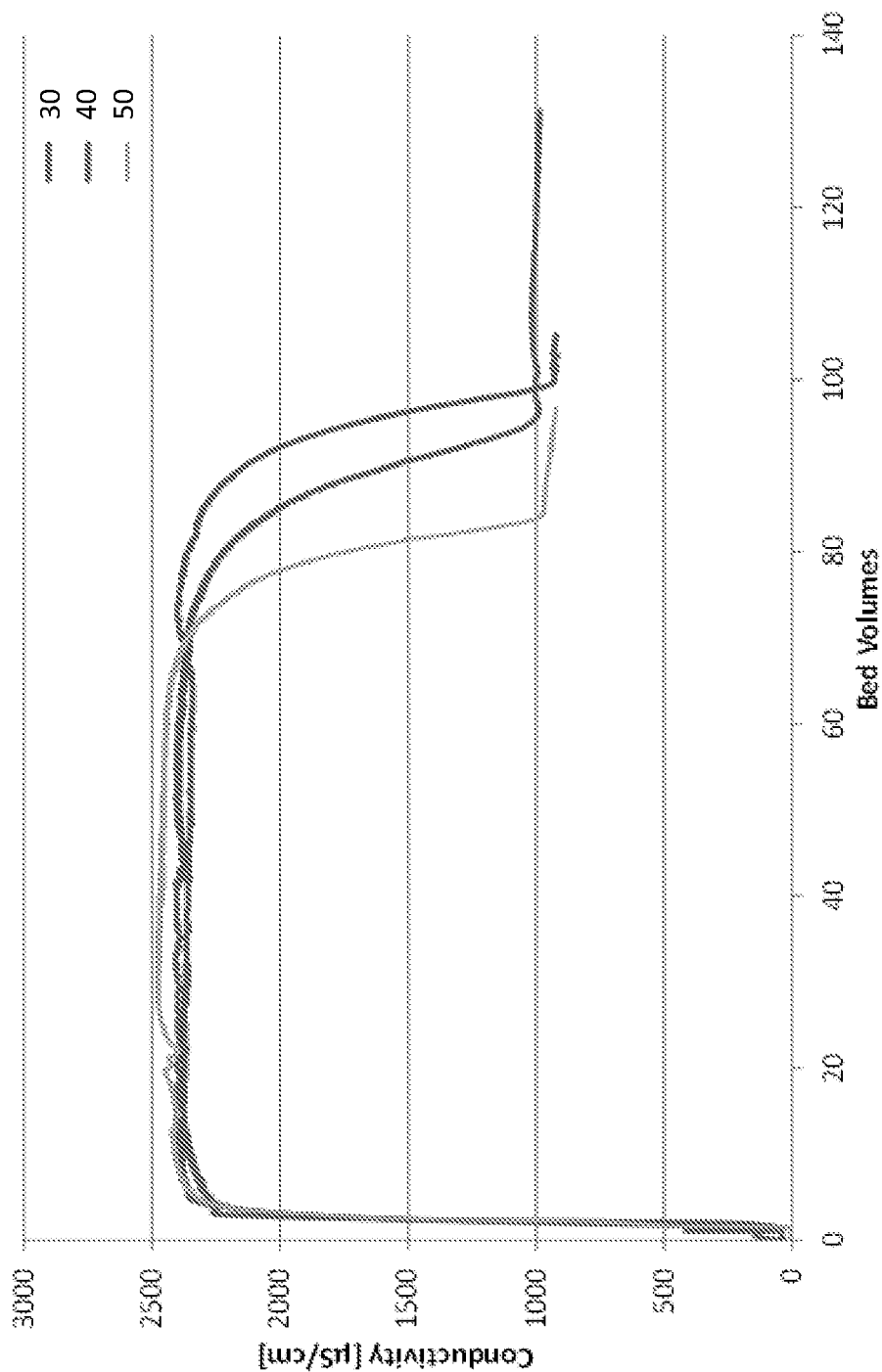
FIG. 2 is a graphical illustration of test results obtained using a strongly basic anion exchange resin.

FIG. 2 shows breakthrough curves for three successive loading cycles using 120 mL of fresh (1$^{st}$ run, line 30) or regenerated (2$^{nd}$ and 3$^{rd}$ cycle, line 40 and 50, respectively) resin. The test solution was the same as described in Example 1, its pH 5, the temperature 50° C. and the feed rate 25 BV/h. The specific conductivity of the eluate is expressed in microSiemens per centimeter, µS/cm.

FIG. 2 shows that the onset of breakthrough does not occur before approximately 70 BV. Further, it follows from FIG. 2 that similar results are obtained with fresh resin and resin regenerated using common methods known to those skilled in the art.

The methods disclosed herein include at least the following embodiments:

Embodiment 1

A method for recovering water from purified terephthalic acid production wastewater, comprising: producing purified terephthalic acid comprising purified terephthalic acid feedstock and wastewater comprising impurities; separating the purified terephthalic acid feedstock from the wastewater comprising impurities; transferring the wastewater to a tank; adjusting the pH of the wastewater with a basic solution; adjusting the temperature of the wastewater; passing the wastewater to a column; contacting the wastewater with an ion exchange resin to remove the impurities; and recovering the water depleted of impurities.

Embodiment 2

The method of Embodiment 1, wherein the pH of the wastewater is adjusted to 4 to 10 with the basic solution.

Embodiment 3

The method of Embodiment 2, wherein the pH of the wastewater is adjusted to 5 to 9.

Embodiment 4

The method of any of Embodiments 1-3, wherein the basic solution is selected from sodium hydroxide, potassium hydroxide, or a combination comprising at least one of the foregoing.

Embodiment 5

The method of any of Embodiments 1-4, wherein the wastewater is contacted with the ion exchange resin at a temperature of 10° C. to 60° C.

Embodiment 6

The method of Embodiment 5, wherein the wastewater is contacted with the ion exchange resin at a temperature of 25° C. to 50° C.

Embodiment 7

The method of any of Embodiments 1-6, wherein the wastewater is a first-stage filtrate emanating from PTA production.

Embodiment 8

A method for recovering water from purified terephthalic acid production wastewater, comprising: producing purified terephthalic acid comprising purified terephthalic acid feedstock and wastewater comprising impurities; separating the purified terephthalic acid feedstock from the wastewater comprising impurities; transferring the wastewater to a tank; adjusting the pH of the wastewater to 5 to 9 with a basic solution; adjusting the temperature of the wastewater to 25 to 50° C.; passing the wastewater to a column; contacting the wastewater with an ion exchange resin to remove the impurities; and recovering the water depleted of impurities.

Embodiment 9

The method of any of Embodiments 1-8, wherein the wastewater comprises impurities selected from para-toluic acid, trimellitic acid, terephthalic acid, ortho-phthalic acid, benzoic acid, acetic acid, 4-carboxybenzaldehyde or a combination comprising at least one of the foregoing.

Embodiment 10

The method of any of Embodiments 1-9, further comprising regenerating the ion exchange resin with the basic solution, wherein the basic solution is selected from sodium hydroxide, sodium carbonate, ammonia, potassium hydroxide, potassium carbonate, or a combination comprising at least one of the foregoing.

Embodiment 11

The method of any of Embodiments 1-10, wherein the ion exchange resin comprises a weakly basic or a strongly basic anion exchange resin.

Embodiment 12

The method of Embodiment 11, wherein the ion exchange resin comprises a matrix comprising polystyrene, aliphatic polyamine, mixed polyalkylene amine, styrene divinyl benzene copolymers, resins containing amine functional groups, resins containing amine derivatives, or combination comprising at least one of the foregoing.

Embodiment 13

The method of any of Embodiments 1-12, wherein the water depleted of impurities contains 1 ppm to 100 ppm acidic impurities.

Embodiment 14

The method of any of Embodiments 1-13, wherein the water depleted of impurities contains 0.1 ppm to 10 ppm para-toluic acid.

Embodiment 15

The method of any of Embodiments 1-14, wherein the water depleted of impurities contains 1 ppm to 10 ppm benzoic acid.

Embodiment 16

The method of any of Embodiments 1-15, wherein the water depleted of impurities contains 1 ppm to 100 ppm acetic acid.

Embodiment 17

The method of any of Embodiments 1-16, wherein the water depleted of impurities comprises 30% to 80% less acidic impurities after contact with the ion exchange resin.

Embodiment 18

The method of Embodiment 17, wherein the water depleted of impurities contains at least 99.5% less acidic impurities as compared to wastewater not treated with an ion exchange resin.

Embodiment 19

The method of any of Embodiments 1-18, wherein the method is conducted at a pressure of 0.1 MegaPascal to 0.3 MegaPascal.

Embodiment 20

The method of any of Embodiments 1-19, wherein the ion exchange resin separates aromatic carboxylic acids from aliphatic carboxylic acids.

Embodiment 21

The method of any of Embodiments 1-20, wherein the ion exchange resin separates aromatic or aliphatic monoacids from di/tri acids containing an aromatic moiety.

Embodiment 22

The method of Embodiment 21, wherein the aromatic carboxylic acids comprise para-toluic acid, trimellitic acid, terephthalic acid, orthophthalic acid, and benzoic acid, or a combination comprising at least one of the foregoing.

Embodiment 23

The method of Embodiment 21, wherein the aliphatic acids comprise acetic acid, acrylic acid, propionic acid, or a combination comprising at least one of the foregoing.

Embodiment 24

A method for recovering water from purified terephthalic acid production wastewater, comprising: producing purified terephthalic acid comprising purified terephthalic acid feedstock and wastewater comprising impurities selected from para-toluic acid, trimellitic acid, terephthalic acid, orthophthalic acid, benzoic acid, acetic acid, or a combination comprising at least one of the foregoing; separating the purified terephthalic acid feedstock from the wastewater comprising impurities; transferring the wastewater to a tank; adjusting the pH of the wastewater to 5 to 9; adjusting the temperature of the wastewater to 25° C. to 50° C.; passing the wastewater to a column; contacting the wastewater with an ion exchange resin to remove the impurities; recovering the water depleted of impurities, wherein the water depleted of impurities contains at least 99% less acidic impurities as compared to wastewater not treated with an ion exchange resin; regenerating the ion exchange resin with dilute sodium hydroxide; wherein the method is carried out at a pressure of 0.1 MegaPascal to 0.3 MegaPascal.

Embodiment 25

The method of Embodiment 24, wherein the water depleted of impurities contains 1 ppm to 100 ppm acidic impurities.

Embodiment 26

The method of Embodiment 24 or Embodiment 25, wherein the water depleted of impurities contains at least 99.5% less acid impurities as compared to wastewater not treated with an ion exchange resin.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method for recovering water from purified terephthalic acid (PTA) production wastewater, comprising:
    separating purified terephthalic acid from the PTA production wastewater to provide separated wastewater comprising an impurity selected from para-toluic acid, trimellitic acid, terephthalic acid, ortho-phthalic acid, benzoic acid, acetic acid, 4-carboxybenzaldehyde, or a combination comprising at least one of the foregoing;
    transferring the separated wastewater to a tank;
    adjusting the pH of the separated wastewater to a pH of 4 to 10 with a basic solution;
    adjusting the temperature of the separated wastewater;
    passing the separated wastewater to a column;
    contacting the separated wastewater with an ion exchange resin to remove the impurity from the separated wastewater;
    tuning contacting of the separated wastewater with the ion exchange resin by varying hydraulic parameters or selection of the ion exchange resin to
        separate aromatic carboxylic acids from aliphatic carboxylic acids; and/or
        separate aromatic or aliphatic monoacids from di/tri acids containing an aromatic moiety; and
    recovering water depleted of the impurity.

2. The method of claim 1, wherein the pH of the separated wastewater is adjusted to a pH of 5 to 9 with the basic solution.

3. The method of claim 1, wherein the basic solution is selected from sodium hydroxide, potassium hydroxide, or a combination comprising at least one of the foregoing.

4. The method of claim 1, wherein the separated wastewater is contacted with the ion exchange resin at a separated wastewater temperature of 10° C. to 60° C.

5. The method of claim 1, wherein the separated wastewater is a first-stage filtrate emanating from PTA production.

6. A method for recovering water from purified terephthalic acid (PTA) production wastewater, comprising:
    separating purified terephthalic acid from the PTA production wastewater to provide separated wastewater comprising an impurity selected from para-toluic acid, trimellitic acid, terephthalic acid, ortho-phthalic acid, benzoic acid, acetic acid, 4-carboxybenzaldehyde, or a combination comprising at least one of the foregoing;
    transferring the separated wastewater to a tank;
    adjusting the pH of the separated wastewater to a pH of 5 to 9 with a basic solution;
    adjusting the temperature of the separated wastewater to 30 to 45° C.;
    passing the separated wastewater to a column;
    contacting the separated wastewater with an ion exchange resin to remove the impurity from the separated wastewater;
    tuning contacting of the separated wastewater with the ion exchange resin by varying hydraulic parameters or selection of the ion exchange resin to
        separate aromatic carboxylic acids from aliphatic carboxylic acids; and/or
        separate aromatic or aliphatic monoacids from di/tri acids containing an aromatic moiety; and
    recovering water depleted of the impurity.

7. The method of claim 1, further comprising regenerating the ion exchange resin with the basic solution, wherein the basic solution is selected from sodium hydroxide, sodium carbonate, ammonia, potassium hydroxide, potassium carbonate, or a combination comprising at least one of the foregoing.

8. The method of claim 1, wherein the ion exchange resin comprises a matrix comprising polystyrene, aliphatic polyamine, mixed polyalkylene amine, styrene divinyl benzene copolymers, resins containing amine functional groups, resins containing amine derivatives, or combination comprising at least one of the foregoing.

9. The method of claim 1, wherein the water depleted of the impurity contains 1 ppm to 100 ppm of the impurity.

10. The method of claim 1, wherein the water depleted of the impurity contains 0.1 ppm to 10 ppm para-toluic acid, and/or wherein the water depleted of the impurity contains 1 ppm to 10 ppm benzoic acid, and/or wherein the water depleted of the impurity contains 1 ppm to 100 ppm acetic acid.

11. The method of claim 1, wherein the water depleted of the impurity comprises 30% to 80% less of the impurity after contact with the ion exchange resin.

12. The method of claim 11, wherein the water depleted of the impurity contains at least 99.5% less of the impurity as compared to the separated wastewater.

13. The method of claim 1, wherein the separated wastewater is contacted with the ion exchange resin in the column at a pressure of 0.1 MegaPascal to 0.3 MegaPascal.

14. The method of claim 1, wherein the ion exchange resin separates aromatic carboxylic acids from aliphatic carboxylic acids.

15. The method of claim 1, wherein the ion exchange resin separates aromatic or aliphatic monoacids from di/tri acids containing an aromatic moiety.

16. The method of claim 15, wherein the aliphatic acids comprise acetic acid, acrylic acid, propionic acid, or a combination comprising at least one of the foregoing.

17. A method for recovering water from purified terephthalic acid (PTA) production wastewater, comprising:
    separating purified terephthalic acid from t PTA production wastewater to provide separated wastewater comprising an impurity selected from para-toluic acid, trimellitic acid, terephthalic acid, orthophthalic acid, benzoic acid, acetic acid, or a combination comprising at least one of the foregoing;
    transferring the separated wastewater to a tank;
    adjusting the pH of the separated wastewater to a pH of 5 to 9;
    adjusting the temperature of the separated wastewater to 25° C. to 50° C.;
    passing the separated wastewater to a column;
    contacting the separated wastewater with an ion exchange resin to remove the impurity from the separated wastewater;
    tuning contacting of the separated wastewater with the ion exchange resin by varying hydraulic parameters or selection of the ion exchange resin to separate aromatic carboxylic acids from aliphatic carboxylic acids; and/or separate aromatic or aliphatic monoacids from di/tri acids containing an aromatic moiety;

recovering water depleted of the impurity, which contains at least 99% less of the impurity as compared to the separated wastewater; and regenerating the ion exchange resin with dilute sodium hydroxide;

wherein the separated wastewater is contacted with the ion exchange resin in the column at a pressure of 0.1 MegaPascal to 0.3 MegaPascal.

18. The method of claim 17, wherein the water depleted of the impurity contains 1 ppm to 100 ppm of the impurity.

19. The method of claim 17, wherein the water depleted of the impurity contains at least 99.5% less of the impurity as compared to the separated wastewater.

20. The method of claim 1, wherein tuning contacting of the separated wastewater with the ion exchange resin to separate aromatic carboxylic acids from aliphatic carboxylic acids; separate aromatic or aliphatic monoacids from di/tri acids containing an aromatic moiety; or a combination comprising at least one of the foregoing comprises varying hydraulic parameters.

* * * * *